US010877023B2

(12) United States Patent
Ruland et al.

(10) Patent No.: US 10,877,023 B2
(45) Date of Patent: Dec. 29, 2020

(54) DUAL SENSOR TYPES IN BREATH ALCOHOL DETECTION

(71) Applicant: Consumer Safety Technology, LLC, Des Moines, IA (US)

(72) Inventors: Scott Ruland, Kansas City, MO (US); Douglas Edward DeVries, Johnston, IA (US)

(73) Assignee: Consumer Safety Technology, LLC, Des Moines, IA (US)

(*) Notice: Subject to any disclaimer, the term of this patent is extended or adjusted under 35 U.S.C. 154(b) by 86 days.

(21) Appl. No.: 16/156,538

(22) Filed: Oct. 10, 2018

(65) Prior Publication Data

US 2019/0113502 A1    Apr. 18, 2019

Related U.S. Application Data

(60) Provisional application No. 62/571,548, filed on Oct. 12, 2017.

(51) Int. Cl.
*G01N 33/497* (2006.01)
*B60K 28/06* (2006.01)

(52) U.S. Cl.
CPC ....... *G01N 33/4972* (2013.01); *B60K 28/063* (2013.01)

(58) Field of Classification Search
CPC ................ G01N 33/4972; B60K 28/063
See application file for complete search history.

(56) References Cited

U.S. PATENT DOCUMENTS 4,749,553 A * 6/1988 Lopez ............... G01N 33/4972
                                                    180/272
5,048,321 A * 9/1991 Chow ............... G01N 33/4972
                                                    422/84

(Continued)

FOREIGN PATENT DOCUMENTS

CN    204037354     12/2014
CN    104634951     5/2015

(Continued)

OTHER PUBLICATIONS https://romanolawpc.com/wp-content/uploads/2016/11/romano-law-oregon-intoxilyzer-8000-operators-guide-2006-09-08.pdf (Year: 2006).*

(Continued)

*Primary Examiner* — Darlene P Condra
(74) *Attorney, Agent, or Firm* — Pauly, DeVries Smith & Deffner LLC (57) ABSTRACT

Embodiments include breath intoxicant monitoring systems and methods of operating a breath intoxicant monitoring system. In an embodiment, a breath intoxicant monitoring system, includes a first detection element, a second detection element, and a control module. The first detection element can be operable to detect a level of an intoxicant in a user's breath and to provide a continuous signal indicating the level of intoxicant. The second detection element can be operable to detect a level of the intoxicant. The second detection element includes a different type of element than the first detection element. The second detection element can have greater accuracy than the first detection element. The control module to selectively operate the second detection element based on the signal received from the first detection element, and to indicate whether the level of intoxicant in the user's breath exceeds a threshold. Other embodiments are also included herein.

17 Claims, 9 Drawing Sheets

(56) References Cited

U.S. PATENT DOCUMENTS

| | | | |
|---|---|---|---|
| 5,426,415 A * | 6/1995 | Prachar | B60K 28/063 340/576 |
| 6,853,956 B2 | 2/2005 | Ballard et al. | |
| 7,287,617 B2 | 10/2007 | Mobley et al. | |
| 7,299,890 B2 | 11/2007 | Mobley et al. | |
| 7,377,352 B2 | 5/2008 | Mobley et al. | |
| 7,481,292 B2 | 1/2009 | Mobley et al. | |
| 7,934,577 B2 | 5/2011 | Devries et al. | |
| 8,174,394 B2 | 5/2012 | Ridder et al. | |
| 8,179,271 B2 | 5/2012 | Kamiki | |
| 8,256,286 B2 | 9/2012 | Carroll et al. | |
| 8,370,027 B2 | 2/2013 | Pettersson et al. | |
| 8,515,506 B2 | 8/2013 | Ridder et al. | |
| 8,581,697 B2 | 11/2013 | Ridder et al. | |
| 8,981,942 B2 | 3/2015 | He et al. | |
| 9,290,174 B1 * | 3/2016 | Zagorski | B60W 30/09 |
| 9,324,224 B2 | 4/2016 | Schumacher | |
| 9,326,713 B2 | 5/2016 | Bellehumeur et al. | |
| 9,442,103 B1 | 9/2016 | Goad | |
| 2003/0109795 A1 * | 6/2003 | Webber | A61B 5/0836 600/543 |
| 2004/0239510 A1 * | 12/2004 | Karsten | B60K 28/063 340/576 |
| 2005/0087382 A1 | 4/2005 | Bellehumeur | |
| 2005/0251060 A1 * | 11/2005 | Gollar | A61B 5/097 600/532 |
| 2006/0237254 A1 | 10/2006 | Mobley et al. | |
| 2007/0144812 A1 * | 6/2007 | Stewart | B60K 28/063 180/272 |
| 2008/0061238 A1 | 3/2008 | Hok et al. | |
| 2008/0117405 A1 | 5/2008 | Ridder et al. | |
| 2008/0120052 A1 | 5/2008 | Ridder et al. | |
| 2008/0316037 A1 | 12/2008 | Shoji et al. | |
| 2009/0087920 A1 | 4/2009 | Pettersson et al. | |
| 2009/0278698 A1 | 11/2009 | Kamiki | |
| 2010/0063409 A1 | 3/2010 | Hoek | |
| 2010/0268425 A1 | 10/2010 | Pettersson et al. | |
| 2011/0009765 A1 * | 1/2011 | Gollar | A61B 5/097 600/532 |
| 2011/0178420 A1 | 7/2011 | Ridder et al. | |
| 2011/0282167 A1 | 11/2011 | Ridder et al. | |
| 2012/0197096 A1 | 8/2012 | Ridder et al. | |
| 2013/0110311 A1 | 5/2013 | Ver et al. | |
| 2013/0231871 A1 * | 9/2013 | Hok | A61B 5/087 702/19 |
| 2013/0317328 A1 | 11/2013 | Ridder et al. | |
| 2014/0061043 A1 * | 3/2014 | Stock | G01N 33/497 204/403.01 |
| 2014/0155760 A1 | 6/2014 | Ridder et al. | |
| 2014/0171759 A1 | 6/2014 | White et al. | |
| 2014/0180500 A1 * | 6/2014 | Hannon | H04K 3/415 701/2 |
| 2014/0377877 A1 | 12/2014 | Burgi et al. | |
| 2015/0051807 A1 | 2/2015 | Desai et al. | |
| 2015/0219620 A1 | 8/2015 | Hok et al. | |
| 2015/0233897 A1 | 8/2015 | Hok et al. | |
| 2015/0244452 A1 | 8/2015 | Grohman et al. | |
| 2015/0251660 A1 * | 9/2015 | Nelson | B60K 28/063 340/576 |
| 2016/0054297 A1 * | 2/2016 | Barbetta | A61B 5/082 73/23.3 |
| 2016/0146780 A1 | 5/2016 | Granstam et al. | |
| 2016/0356764 A1 | 12/2016 | Martin et al. | |
| 2017/0101006 A1 | 4/2017 | Devries et al. | |
| 2017/0101007 A1 | 4/2017 | Devries et al. | |
| 2017/0184537 A1 * | 6/2017 | Umasankar | G01N 27/4074 |
| 2018/0266985 A1 * | 9/2018 | Farhad | G01N 27/4074 |

FOREIGN PATENT DOCUMENTS

| | | |
|---|---|---|
| DE | 3119341 | 12/1982 |
| EP | 0310672 | 4/1989 |
| EP | 1874578 | 7/2010 |
| EP | 2212147 | 8/2010 |
| EP | 2389100 | 5/2013 |
| EP | 2486403 | 6/2013 |
| GB | 2442980 | 4/2008 |
| GB | 2468522 | 8/2013 |
| JP | 0650918 | 2/1994 |
| JP | 2008232710 | 10/2008 |
| JP | 5154112 | 12/2012 |
| WO | 2006130129 | 12/2006 |
| WO | 2007094712 | 8/2007 |
| WO | 2010085716 | 7/2010 |
| WO | 2014031071 | 2/2014 |
| WO | 2014031072 | 2/2014 |
| WO | 2015181835 | 12/2015 |
| WO | 2016113353 | 7/2016 |

OTHER PUBLICATIONS https://www.bactrack.com/blogs/expert-center/35043845 (Year: 2015).*

"Breath Alcohol Sensors," Datasheet for Dart Sensors Revised Sep. 20, 2016 (8 pages).

"Fuel Cell Sensors," Product Descriptions for Quad Cell and Standard Cell Sensors Retrieved from http://www.fuelcell-sensors.com Feb. 14, 2017 (14 pages).

"Operating Principle," for Figaro Sensors retrieved from http://www.figarosensor.com/technicalinfo/principle/mos-type.html on Feb. 14, 2017 (5 pages).

"Product Descriptions," for Alcohol and Carbon Monoxide Sensors produced by Dart Sensors retrieved from www.dart-sensors.com on Feb. 14, 2017 (5 pages).

* cited by examiner

DUAL SENSOR TYPES IN BREATH ALCOHOL DETECTION

This application claims the benefit of U.S. Provisional Application No. 62/571,548, filed Oct. 12, 2017, the contents of which are herein incorporated by reference.

FIELD OF THE TECHNOLOGY

The present application relates generally to breath alcohol monitoring devices. More specifically, the present application relates to breath alcohol monitoring devices with multiple detection elements.

BACKGROUND

Vehicles incorporate breath alcohol ignition interlock devices, sometimes abbreviated as BAIIDs, to prevent a driver with a known history of driving while intoxicated with alcohol from operating the vehicle while intoxicated. Such devices are designed to prevent a driver from starting a motor vehicle when the driver's breath alcohol concentration (BAC) is at or above a set alcohol concentration. Each state in the U.S. has adopted a law providing for use of such BAIID devices as a sanction for drivers convicted of driving while intoxicated, or as a condition of restoring some driving privileges after such offenses.

A typical BAIID device meets guidelines established by the National Highway Traffic Safety Administration (NHTSA) in published model specifications for BAIIDs, which specify various features and safeguards that should be present in such a device to make it an effective and reliable deterrent to intoxicated driving. For example, the model specifies a volume of air in a breath that the driver provides to ensure that an adequate volume of air to ensure an accurate result is provided, and specifies how such a device should be installed into a vehicle to prevent the vehicle from operating pending a determination that the driver is not intoxicated. Most state programs and manufacturer BAIID products adhere to the NHTSA model guidelines, providing a uniform market for various brands of BAIID products.

In operation, a driver must use a BAIID device by blowing into an alcohol-sensing element such as a fuel cell that measures the amount of alcohol in the driver's breath. The BAIID reads a signal from the fuel cell or other alcohol-sensing element, and determines whether the driver's blood alcohol content exceeds a threshold amount, based on a known relationship between blood alcohol and breath alcohol. If the driver's determined blood alcohol content does not exceed the threshold, the BAIID allows the vehicle to start and run by electrically enabling a system within the vehicle, such as the starter, fuel pump, ignition, or the like. If the driver's blood alcohol concentration exceeds the threshold, the vehicle is not allowed to start, and the BAIID device records a violation.

In addition to ignition interlock devices, other breath intoxicant monitoring systems exist, such as to monitor an individual as directed by a court or to monitor individuals at his/her place of work. BAIIDs make a determinations whether or not a driver is in a condition to operate the vehicle. Other breath intoxicant monitoring systems can make determinations whether an individual is violating a court order or whether an individual is fit perform his/her employment responsibilities. Therefore, it is important that breath intoxicant monitoring systems are able to accurately determine an individual's blood alcohol content. Accordingly, there is a need for more reliable and accurate testing devices and methods.

SUMMARY

One general aspect includes a breath intoxicant monitoring system, including: a first detection element operable to detect a level of an intoxicant in a user's breath, the first detection element operable to provide a continuous signal indicating a level of intoxicant in a user's breath; a second detection element operable to detect a level of the intoxicant in the user's breath, the second detection element including a different type of element than the first detection element, where the second detection element has greater accuracy than the first detection element; and a control module operable to receive a signal from the first and second detection elements indicating the level of intoxicant in the user's breath, to selectively operate the second detection element based on the signal received from the first detection element, and to indicate whether the level of intoxicant in the user's breath measured from at least one of the first and second detection elements exceeds a threshold.

Implementations may include one or more of the following features. The breath intoxicant monitoring system the control module further operable to selectively restrict operation of a vehicle based on whether the level of intoxicant in the user's breath measured from at least one of the first and the second detection elements exceeding a threshold. The breath intoxicant monitoring system where the first detection element includes one of the group including of a metal oxide sensor, a complementary metal oxide sensor, a semiconductor sensor, and an infrared sensor. The breath intoxicant monitoring system where the second detection element includes a fuel cell. The breath intoxicant monitoring system where the control module is operable to measure the signal from the first detection element before taking a sample with the second detection element, and to avoid taking a breath sample using the second detection element if the signal from the first detection element indicates a level of intoxicant in the user's breath exceeding a contamination threshold. The breath intoxicant monitoring system where the control module is operable to measure the signal from the first detection element before taking a sample with the second detection element, and to take a sample using the second detection element when the signal from the first detection element indicates that the breath being sampled is deep lung breath. The breath intoxicant monitoring system where the control module is operable to measure an environment signal from the first detection element to monitor air surrounding the system for contamination before prompting a user to perform a test and taking a sample with the second detection element. The breath intoxicant monitoring system where the control module is further operable to delay a test or a retest if the environment signal exceeds a threshold. The breath intoxicant monitoring system where the breath intoxicant monitoring system includes an ignition interlock system or a home monitoring system. The breath intoxicant monitoring where greater accuracy includes greater specificity to the intoxicant.

One general aspect includes a breath intoxicant monitoring system, including: a first detection element operable to detect a level of an intoxicant in a user's breath, the first detection element operable to provide a signal indicating the level of the intoxicant in the user's breath; a second detection element operable to detect a level of the intoxicant in the user's breath, the second detection element including a fuel cell, where the first detection element is less susceptible to contamination than a fuel cell; and a control module operable to receive a signal from the first and second detection elements indicating a level of intoxicant in the user's breath, to measure the signal from the first detection element before taking a sample with the second detection element and to avoid taking a breath sample using the second detection element if the signal from the first detection element indicates a level of intoxicant in the user's breath that would contaminate the second detection element, and to indicate whether the level of intoxicant in the user's breath measured from at least one of the first and second detection elements exceeds a threshold. Other embodiments of this aspect include corresponding computer systems, apparatus, and computer programs recorded on one or more computer storage devices, each configured to perform the actions of the methods.

Implementations may include one or more of the following features. The breath intoxicant monitoring system where the control module is further operable to selectively restrict operation of a vehicle based on the level of the intoxicant in the user's breath measured from at least one of the first and the second detection elements exceeding a threshold. The breath intoxicant monitoring system where the intoxicant is ethanol, and the first detection element includes a semiconductor sensor. Implementations of the described techniques may include hardware, a method or process, or computer software on a computer-accessible medium.

One general aspect includes a method of operating a breath intoxicant monitoring system, including: detecting a level of an intoxicant in a user's breath using a first detection element operable to provide a continuous signal indicating a level of intoxicant; receiving in a control module a signal from the first detection element indicating the level of intoxicant in the user's breath; selectively operating via the control module a second detection element operable to detect a level of intoxicant in the user's breath based on the signal received from the first detection element, the second detection element including a different type of element than the first detection element, where the second detection element has greater accuracy than the first detection element; and indicating whether the level of intoxicant in the user's breath measured from at least one of the first and second detection elements exceeds a threshold. Other embodiments of this aspect include corresponding computer systems, apparatus, and computer programs recorded on one or more computer storage devices, each configured to perform the actions of the methods.

Implementations may include one or more of the following features. The method of operating a breath intoxicant monitoring system further including selectively restricting operation of a vehicle based on the level of intoxicant in the user's breath measured from at least one of the first and the second detection elements exceeding a threshold. The method of operating a breath intoxicant monitoring system where the intoxicant is ethanol, the first detection element includes a semiconductor sensor, and the second detection element includes a fuel cell. The method of operating a breath intoxicant monitoring system where the second detection element includes a fuel cell, where the first detection element is less susceptible to contamination than a fuel cell, where selectively operating the second detection element includes avoiding taking a breath sample using the second detection element if the signal from the first detection element indicates a level of intoxicant in the user's breath that would contaminate the second detection element. The method of operating a breath intoxicant monitoring system where selectively operating the second detection element includes taking a breath sample using the second detection element when the signal from the first detection element indicates that the breath being sampled is deep lung breath. The method of operating a breath intoxicant monitoring system where the second detection element includes a fuel cell, where the first detection element is less susceptible to contamination than a fuel cell, where selectively operating the second detection element includes measuring an environment signal from the first detection element to monitor air around the system for contamination before prompting the user to perform a test and taking a sample with the second detection element. Implementations of the described techniques may include hardware, a method or process, or computer software on a computer-accessible medium.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

The technology may be more completely understood in connection with the following drawings, in which.

While the technology is susceptible to various modifications and alternative forms, specifics thereof have been shown by way of example and drawings, and will be described in detail. It should be understood, however, that the application is not limited to the particular embodiments described. On the contrary, the application is to cover modifications, equivalents, and alternatives falling within the spirit and scope of the technology.

DETAILED DESCRIPTION

The embodiments of the present technology described herein are not intended to be exhaustive or to limit the technology to the precise forms disclosed in the following detailed description. Rather, the embodiments are chosen and described so that others skilled in the art can appreciate and understand the principles and practices of the present technology.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Various embodiments of the breath intoxicant monitoring systems described herein require two or more detection elements. Each detection element included in the system can be configured to evaluate a sample of air, such as a breath from the user, for a level of intoxicant, which can be correlated to the intoxicant level of the user.

In some embodiments, the first detection element can determine a level of intoxicant in the provided sample. In various embodiments, the second detection element can be a different type of detection element than the first detection element, such as a more accurate detection element.

The system can use the information from the first detection element to determine whether the second detection element should be used to determine the level of intoxicant in the sample. In some embodiments, the system can make the determination to use the second detection element based on the level of intoxicant, such as to prevent contamination of the second detection element. In some embodiments, the system can make the determination to use the second detection element based on when the first detection element determines the breath from the user includes deep lung air. In some embodiments, the system can make the determination to use the second detection element based on the type of intoxicant detected by the first detection element, such as to avoid using the second detection element when the environment surrounding the user would affect the results of the sample or decrease the reliability of the results. The two detection elements can be used together to obtain a more reliable or more accurate reading of the level of intoxicant in the user.

Figure 1:
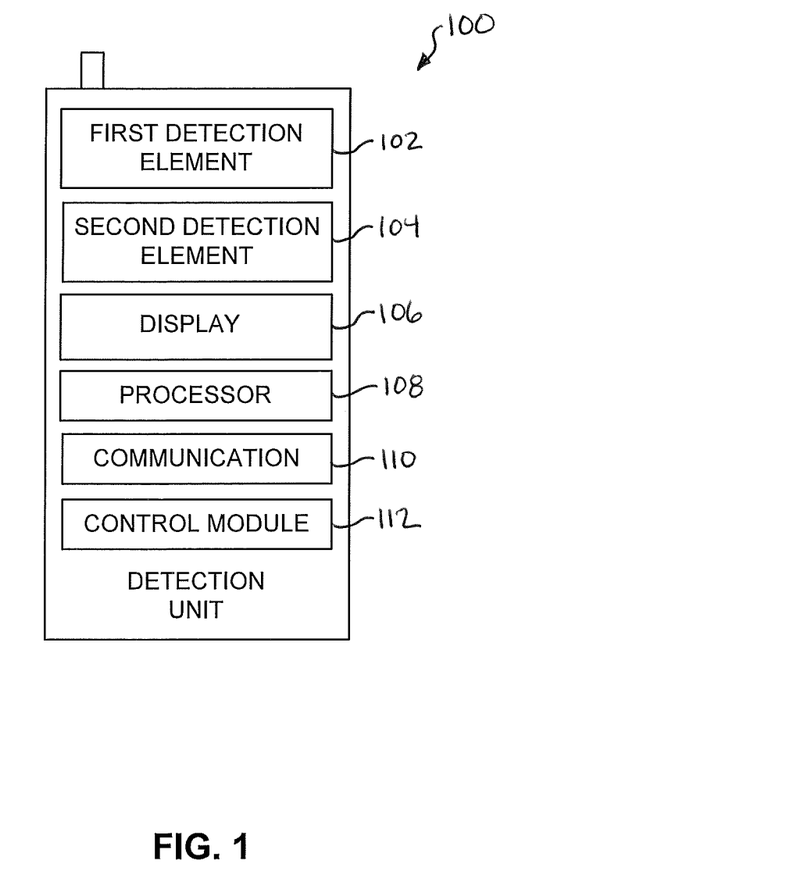
FIG. 1 is a schematic of a breath intoxicant monitoring system, according to an embodiment.

In reference now to the figures, FIG. 1 shows a schematic of detection unit 100 of a breath intoxicant monitoring system, according to an embodiment. The detection unit 100 can include a first detection element 102, a second detection element 104, a display 106, a processor 108, a communication element 110, and a control module 112.

The first detection element 102 can be operable to detect a level of an intoxicant in a user's breath. Various examples of detection elements are discussed below. The first detection element 102 can receive a sample of air, such as the user's breath. The first detection element 102 can analyze the sample of air to determine the level of an intoxicant in the sample. In various embodiments, the intoxicant can include alcohol, such as ethanol.

The first detection element 102 can provide a continuous signal indicating the level of intoxicant in the sample being provided. The signal can be continuous such that the detection element is configured to provide or output the level of intoxicant for the air that just passed through or by the detection element. In some embodiments, the control module 112 can evaluate the continuous signal to differentiate between different portions of the sample. For example when the sample is a user's breath, the initial portion of the sample can have different characteristics than a later portion of the sample, such as when the initial portion of the sample is from the user's mouth and throat and a later portion of the sample is from is deep lung air.

The second detection element 104 can also be operable to detect a level of the intoxicant in the user's breath. The second detection element 104 can be a different type of element than the first detection element 102, such that the manner in which the detection elements detect a level of intoxicant can be fundamentally different, such as an fuel cell compared to an IR sensor. In various embodiments, the second detection element 104 can have a greater accuracy than the first detection element 102. In some embodiments, the first detection element 102 can be less susceptible to contamination than the second detection element 104, such as when the second detection element 104 is a fuel cell.

Examples of detection elements for alcohol in breath that can provide a continuous signal are a complementary metal oxide semiconductor (CMOS) sensor, a metal oxide semiconductor (MOS) sensor, a semiconductor sensor, and an infrared (IR) sensor. These detection elements and detection elements that provide a continuous signal do not need to wait for a predetermined time period after receiving a breath sample to provide a breath alcohol content reading that is considered accurate.

Fuel cell sensors for alcohol in breath do not provide a continuous signal. In fuel cell sensors, an electrochemical process oxidizes the alcohol in a breath sample at a catalytic electrode surface and produces an electrical current that is used to measure the alcohol content. Two electrodes are partitioned by a porous acid-electrolyte material. As exhaled air passes through the fuel cell, the electrode material, such as platinum, oxidizes any alcohol present and produces acetic acid, protons and electrons. The electrons flow through a conductor from the electrodes, are measured, and reveal the breath alcohol content. A period of time is required for the fuel cell to reach the peak output, or maximum voltage or current from the cell after a sample has been introduced. This period of time is referred to as the peak time. Because the fuel cell provides a reading giving the accurate breath alcohol content only after peak time has passed, the fuel cell is not considered to provide a continuous signal. Fuel cell sensors require mechanism to provide a small, fixed volume of the breath sample, such as a pump or injection system. As a result, a fuel cell sensor cannot monitor the expired alcohol concentration curve over time during the course of a breath expiration, such as to distinguish between vapors coming from the mouth and vapors coming from the lung. Also, each fuel cell has a recovery time during which it returns to the steady state voltage or current flow before it received a sample. An advantage of fuel cells alcohol sensors is that they have high analytic specificity to alcohol, they are highly accurate even at low alcohol concentrations, and they have a linear response to alcohol vapor over a wide concentration range. Fuel cell sensors for breath alcohol are available commercially from Fuel Cell Sensors having a place of business in Vale of Glamorgan, Wales, United Kingdom or from Dart Sensors having a place of business in Exeter, England, United Kingdom. Methods for analyzing a gas sample for a substance are described in U.S. Pat. Nos. 5,612,896, 6,596,153, and 6,795,775, which are hereby incorporated by reference in their entireties.

A semiconductor sensor, CMOS sensor, and MOS sensor can include a transition metal oxide material across which a voltage is applied to produce a standing current. The magnitude of the current is affected by the conductivity of the surface of the transition metal oxide material, which can be modified by the presence and concentration of substances in the air around the transition metal oxide material. A heater is provided to maintain the metal oxide material at an appropriate temperature for sensing. When alcohol or a number of other substances come into contact with the metal oxide material, it is adsorbed onto the metal oxide material's surface, changes the surface resistivity, and changes the standing current. The change in current can be used to calculate the concentration of alcohol or the other substances that change the surface resistivity of the metal oxide. Semiconductor sensors do not have a linear response to increasing concentrations of alcohol vapor. In some embodiments, the signal from a semiconductor sensor can be continuous such that the detection element is configured to provide or output the level of intoxicant for the air that just passed through or by the detection element. Semiconductor sensors or MOS sensors are available from Figaro USA Inc. of Arlington Heights, Ill., USA. CMOS sensors are available from Cambridge CMOS Sensors Ltd., a subsidiary of ams AG, of Premstaetten, Austria.

A typical IR sensor includes an inlet area, an inlet area for a breath sample to flow through, an infrared emitter, and a receiver of infrared light for receiving infrared light from the emitter after passing through the breath sample. The IR sensor may be configured to cause the IR light to pass through multiple reflections before reaching the receiver. Alcohol and other substances absorb infrared light at various wavelengths. The quantity of radiation absorbed depends on the concentration of absorbing substances present in the sample. It is possible for an IR sensor to be configured as a continuous flow sensor which is able to track the shape of the alcohol concentration curve over time during the course of a breath expiration, such as to distinguish between vapors coming from the mouth and vapors coming from the lung. The IR sensor may include a sensor for a tracer gas to help determine the concentration of the breath sample compared to the ambient air that is present in the flow path. IR alcohol sensors are available from Lion located at Barry, South Wales, United Kingdom.

The display 106 can show information to the user. In some embodiments, the display 106 can include a screen, such as an LCD screen. In various embodiments, the display 106 can show the user the results of a test, can prompt the user to provide a sample, or can instruct the user on what the next steps are.

Figure 7:
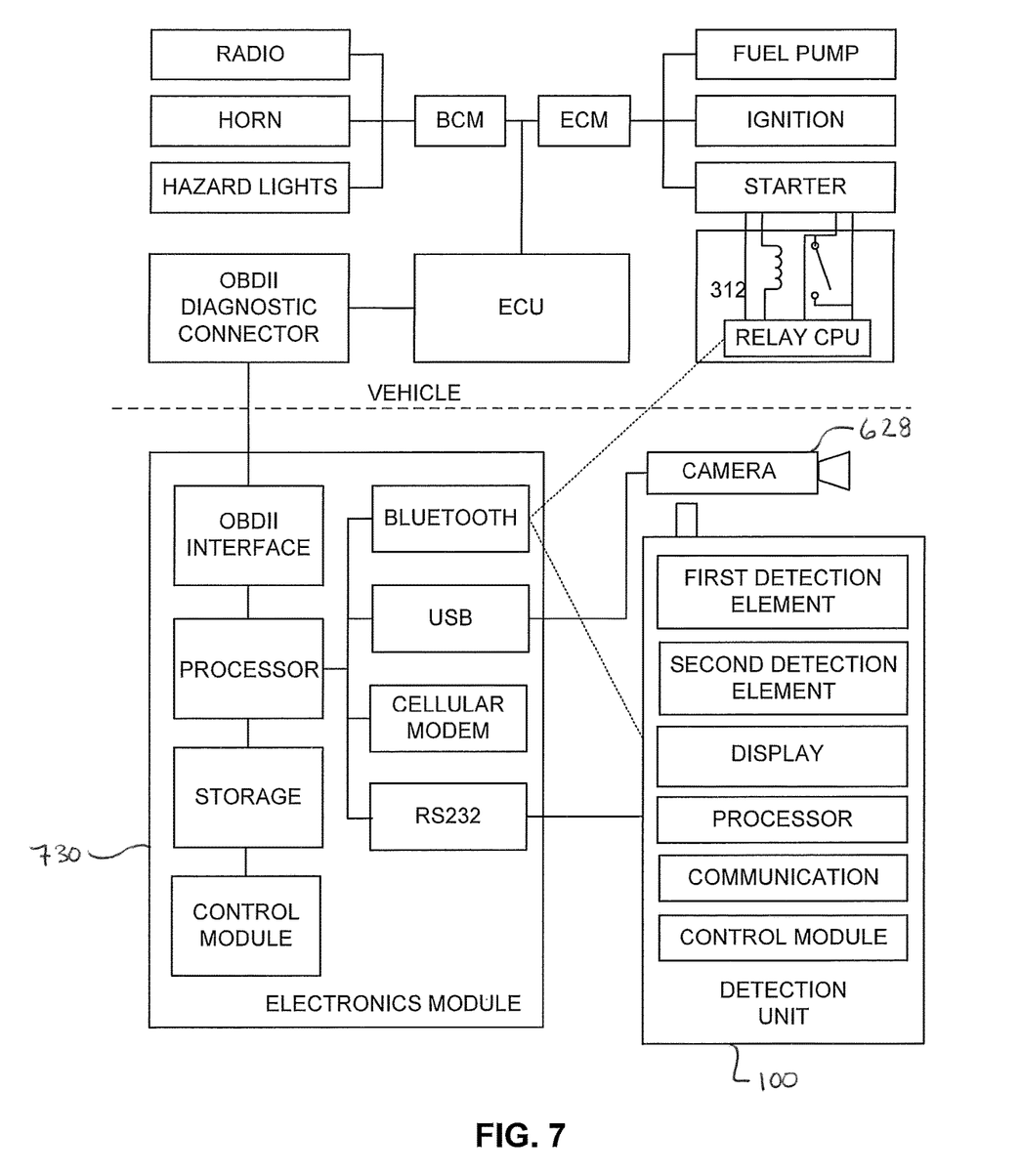
FIG. 7 is a schematic of an intoxicant monitoring system, according to an embodiment.

In various embodiments, the control module 112 can be included in the detection unit 100. In some embodiments, the control module 112 can be included in an electronics module (as shown in FIG. 7). In some embodiments, portions of the control module 112 can be included in the detection unit 100 and portions of the control module can be included in an electronics module.

Figure 2:
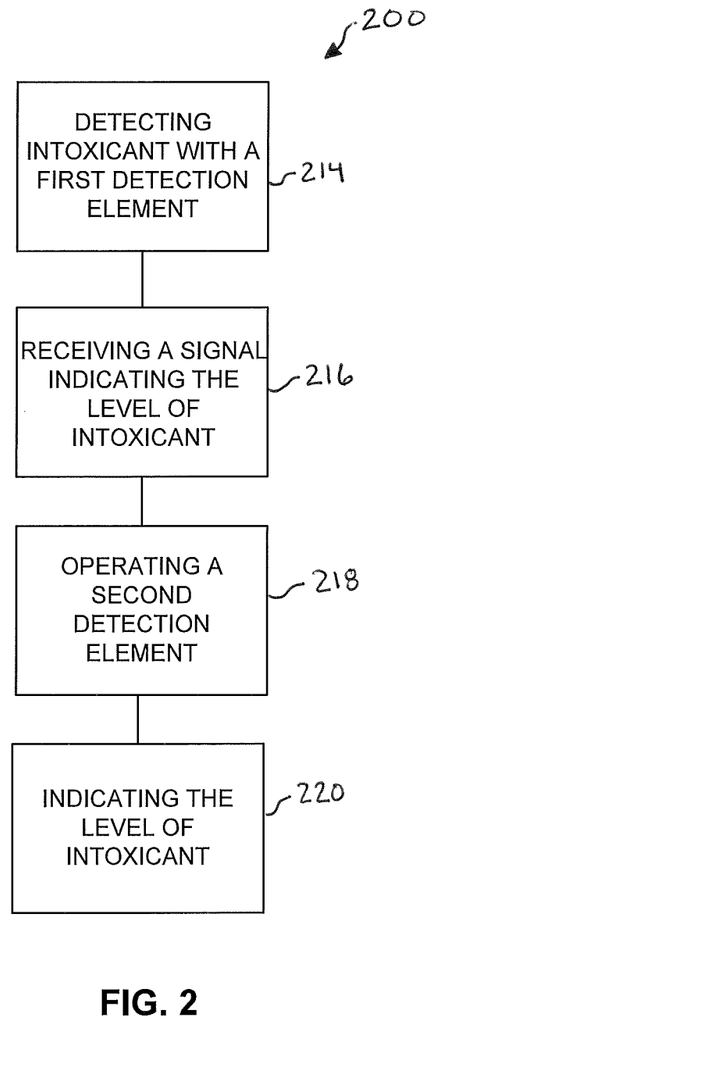
FIG. 2 is a flow chart showing an operation of a breath intoxicant monitoring system, according to an embodiment.

FIG. 2 shows a flow chart showing a method 200 of an operation of a breath intoxicant monitoring system, according to an embodiment. The method 200 can include detecting a level of an intoxicant in a user using a first detection element operable to provide a continuous signal indicating the level of intoxicant in a user's breath, step 214. The control module can receive the signal from the first detection element indicating the level of intoxicant, step 216. The control module can selectively operate the second detection element based on the signal received from the first detection element, step 218. The second detection element can include a different type of detection element than the first detection element. The second type of detection element can have greater accuracy that the first type of detection element. The method 200 can further include indicating whether the level of intoxicant in the user's breath measured from at least one of the first and second detection elements exceeds a threshold, step 220.

In some embodiments, the method 200 can further include selectively restricting operation of the vehicle based on the level of intoxicant in the user's breath measured from the first detection element or the second detection elements, such as if the level of intoxicant exceeds a threshold.

Figure 3:
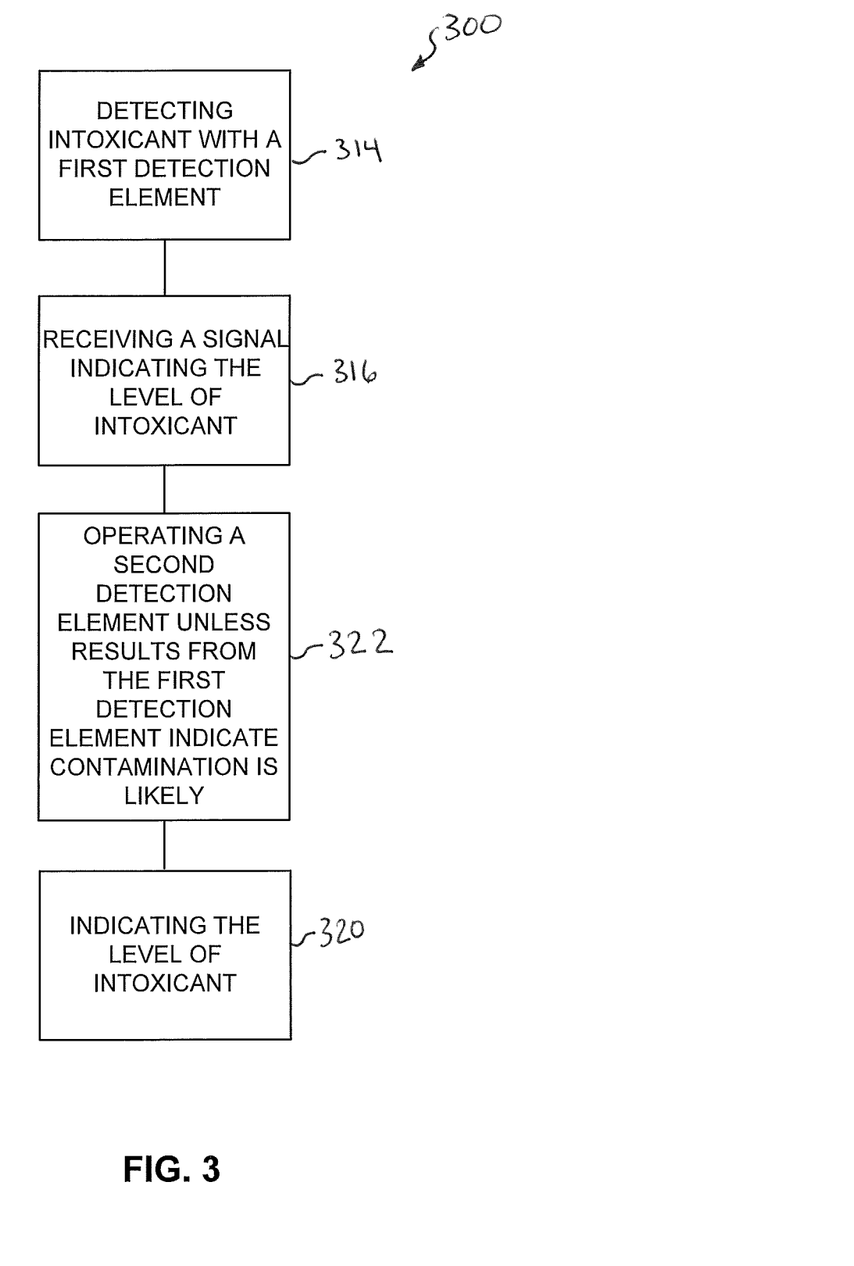
FIG. 3 is a flow chart showing an operation of a breath intoxicant monitoring system, according to an embodiment.

FIG. 3 shows a flow chart showing a method 300 of an operation of a breath intoxicant monitoring system, according to an embodiment. The method 300 can include detecting a level of intoxicant in a user using a first detection element operable to provide a continuous signal indicating the level of intoxicant in a user's breath, step 314. The control module can receive the signal from the first detection element indicating the level of intoxicant, step 316. The control module can selectively operate the second detection element to detect a level of intoxicant in the user's breath based on the signal received from the first detection element, such as to avoid taking a breath sample using the second detection element if the signal from the first detection element indicates a level of intoxicant in the user's breath that would contaminate the second detection element, step 322. The second detection element can include a different type of detection element than the first detection element. The second type of detection element can have a greater accuracy than the first type of detection element.

In some embodiments, the method 300 can further include selectively restricting operation of the vehicle based on the level of intoxicant in the user's breath measured from the first detection element or the second detection elements, such as if the level of intoxicant exceeds a threshold, step 320.

Figure 4:
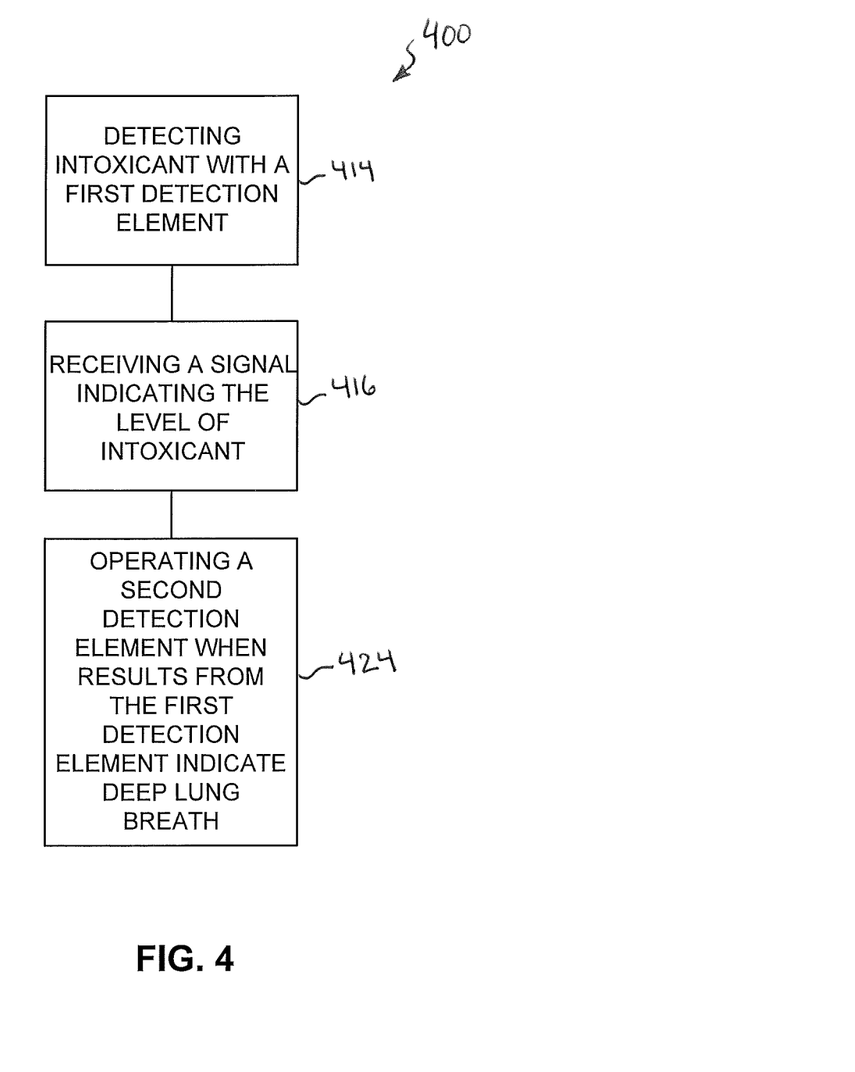
FIG. 4 is a flow chart showing an operation of a breath intoxicant monitoring system, according to an embodiment.

FIG. 4 shows a flow chart showing a method 400 of an operation of a breath intoxicant monitoring system, according to an embodiment. The method 400 can include detecting a level of intoxicant in a user using a first detection element operable to provide a continuous signal indicating the level of intoxicant in a user's breath, step 414. The control module can receive a signal from the first detection element indicating the level of intoxicant, step 416. The control module can selectively operate the second detection element to detect a level of intoxicant in the user's breath based on the signal received from the first detection element, step 424. The control module can be configured to measure the signal from the first detection element before taking a sample with the second element. The control module can be further configured to take a sample using the second element when the signal from the first element indicates that the breath being sampled is deep lung breath. The second detection element can include a different type of element than the first detection element. The second type of detection element can have greater accuracy than the first type of detection element.

In some embodiments, the method 400 can further include selectively restricting operation of the vehicle based on the level of intoxicant in the user's breath measured from the first detection element or the second detection elements, such as if the level of intoxicant exceeds a threshold.

Figure 5:
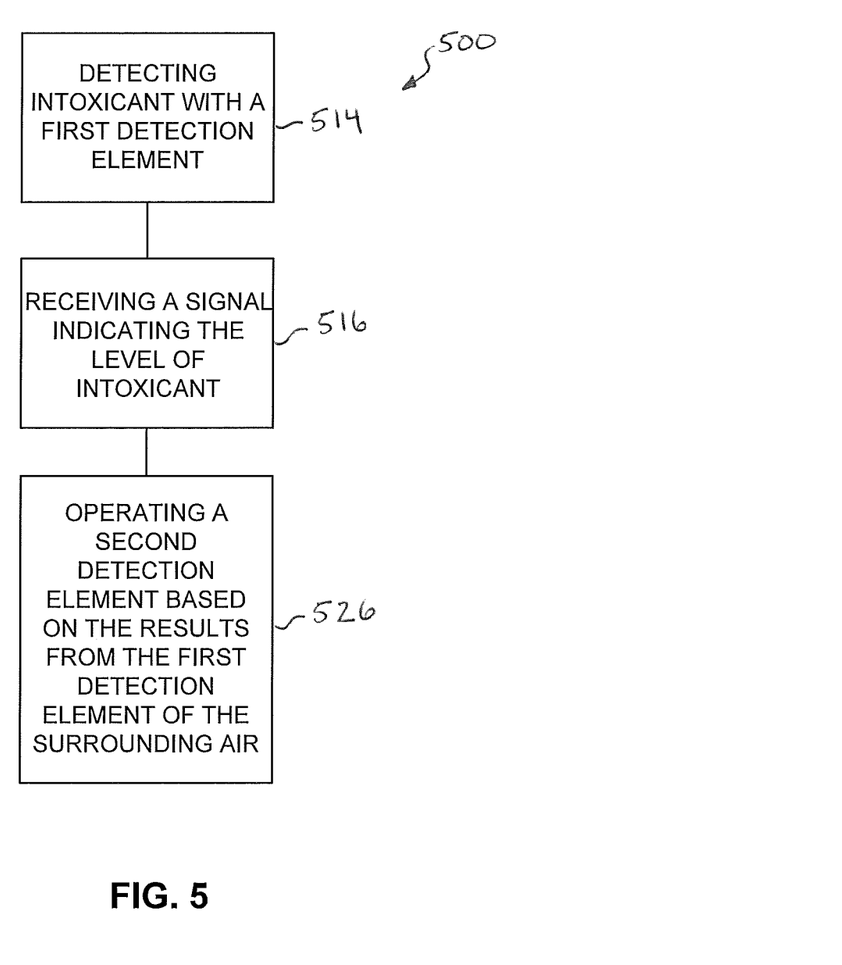
FIG. 5 is a flow chart showing an operation of a breath intoxicant monitoring system, according to an embodiment.

FIG. 5 shows a flow chart showing a method 500 of an operation of a breath intoxicant monitoring system, according to an embodiment. The method 500 can include detecting a level of intoxicant in the environment using a first detection element operable to provide a continuous signal indicating the level of intoxicant in a user's breath, step 514. The control module can receive a signal from the first detection element indicating the level of intoxicant, step 516. The control module can selectively operate the second detection element operable to detect a level of intoxicant in the user's breath based on the signal received from the first detection element, step 526. The control module can be configured to measure an environment signal from the first element indicating the level of intoxicant in the air surrounding the system, such vehicle cabin air, for contamination before prompting the user to perform a test and taking a sample with the second element. The second detection element can include a different type of element than the first detection element. The second type of detection element can have greater accuracy than the first type of detection element. The first detection element to indicate the content of the air in the environment, for example, if the user is located in a room with elevated levels of alcohol present in the air, can reduce the occurrences of a false positive result.

In various embodiments, a first detection element can be used to test environmental air before a second detection element is used to test a user's breath on some occasions. In various embodiments, a first detection element can be used to test environmental air before each use of a second detection element to test a user's breath. In various embodiments, a first detection element can be used to test environmental air after a second detection element indicates that a user has a breath alcohol over a threshold.

In some embodiments, the method 500 can further include selectively restricting operation of the vehicle based on the level of intoxicant in the user's breath measured from the first detection element or the second detection elements, such as if the level of intoxicant exceeds a threshold.

Figure 6:
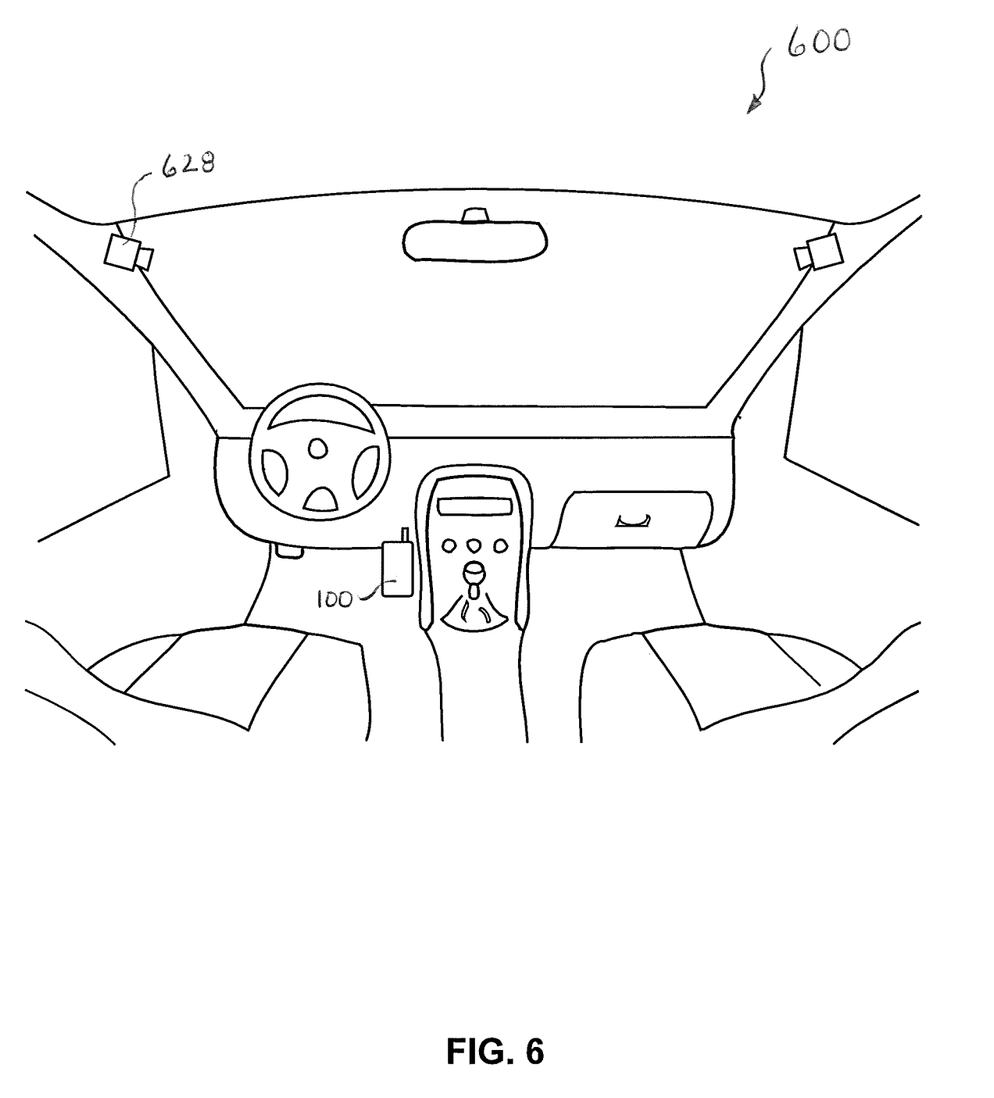
FIG. 6 is a portion of a vehicle interior as may be used with various embodiments.

FIG. 6 shows a portion of a vehicle interior as may be used with various embodiments described herein. Here, the interior of a car 600 includes a driver's seat on the left, a front passenger seat on the right, a steering wheel, and other common elements of a typical car interior. The vehicle further includes a BAIID handheld or detection unit 100, configured to selectively enable vehicle operation based on a driver's intoxication state. The BAIID system can also include one or more cameras 628 to monitor or capture images of the vehicle interior, such as to be reviewed by a governing body. The detection unit 100 is typically coupled to a control box or relay box which can be part of the BAIID system, linking the detection unit to one or more vehicle systems such as the starter motor, fuel pump, ignition circuit, lights, horn, diagnostic link connector (DLC) or on-board diagnostic II (OBD-II) connector, and other such vehicle systems. In an example of a BAIID system discussed in greater detail in U.S. patent application Ser. No. 15/223,894, filed Jul. 29, 2016, and titled "Diagnostic Port Intoxication Vehicle Immobilization," to DeVries et al. and hereby incorporated by reference, the BAIID can control the vehicle through an Onboard Diagnostic port of the vehicle.

In operation, a user is unable to start the vehicle using the ignition key without first blowing a breath sample into the handheld detection unit 100 that indicates the user is not intoxicated. The handheld detection unit 100 determines the amount of alcohol in the user's breath using the first and second detection elements or other device operable to quantify the amount of ethanol in a breath sample, and signals the relay box or electronics module (shown in FIG. 7) to enable normal operation of the vehicle if the user's breath has an ethanol concentration below a specified threshold. The electronics module responds to the signal by bringing one or more vehicle systems to a normal operational state, such as by enabling a starter motor or fuel pump relay to receive a control signal to start or run the vehicle.

In another example of a BAIID system, discussed in greater detail in U.S. patent application Ser. No. 15/223,921, filed Jul. 29, 2016, and titled "Networked Intoxication Vehicle Immobilization," to DeVries et al. and hereby incorporated by reference, the electronics unit or handheld detection unit can be operable to use wireless communication to interact with relays or other such devices controlling operation of the vehicle. In a more detailed example, the electronics module can be mounted under the dash of the vehicle and uses Bluetooth wireless communication signals to communicate with a wireless relay that is inserted into one or more vehicle systems, or that replaces a traditional relay that controls one or more vehicle systems. This example provides a significant benefit of reducing installation time and reducing permanent alteration to the user's vehicle incurred when a traditional BAIID is installed using hard-wired components. In various examples, the wireless components can communicate using wireless communication protocol, such as Bluetooth. The term "Bluetooth" is used herein to indicate that a component is capable of communicating according to a standard for wireless exchange of data over short distances, such as by using short-wavelength UHF radio waves in the industrial, scientific and medical (ISM) band from 2.4-2.485 Gigahertz. Standards for Bluetooth communication are managed by the Bluetooth Special Interest Group.

FIG. 7 shows an example BAIID device incorporating an electronics module. Here, the vehicle components shown above the dotted line show typical vehicle elements such as an engine control unit (ECU), body control module (BCM), and engine control module (ECM) which electronically control vehicle components. The BCM controls vehicle accessories such as the radio, horn, and lights, while the ECM controls engine-specific components such as the fuel pump, ignition, and starter. A Bluetooth wireless relay is shown coupled to the starter, such that the relay is normally disabled but can be enabled by the BAIID's control module using a Bluetooth signal. The control module or electronics module can thereby be operable to selectively enable the starter, and therefore the vehicle, based on successful completion of an intoxicant test such as breath alcohol test.

The electronics module 730 can include various components enabling the device to work as a breath alcohol (or other intoxicant) ignition interlock, including a wired and/or wireless interface to vehicle systems, a processor, storage, USB or RS232 ports, and a cellular modem. The electronics module 730 can be coupled to a detection unit 100 which can include the first detection element, the second detection element and a display, as well as a processor, a communications module for communication with the electronics module, and other such components. In an alternate example, functions of the electronics module 730 and detection unit 100 are contained in the same housing or unit, such as a single handheld unit in place of the electronics module and detection unit pictured here.

In some embodiments, the electronics module 730 can include a cellular modem, or a connection to an external cellular telephone, such as a user-provided Bluetooth smart phone. In other examples, the connection between the external cellular telephone and the electronics module will be a Near-Field Communication (NFC) connection, a Wi-Fi connection, another wireless connection, or a wired or tethered connection. The electronics module can be operable to communicate data, such as test results, diagnostics, images or video, and other such information to a remote server via the cellular modem, and if the external cellular telephone is communicatively coupled to the electronics module, via the external cellular telephone.

As used herein, in some embodiments, the term cellular telephone can be interchanged with the term cellular modem and terms describing devices that provide the ability to communicate with a remote server. In some embodiments, the term "telephone" indicates that ability to convert acoustic vibrations to electrical signals in order to transmit sound, such as voices, over a distance.

Figure 8:
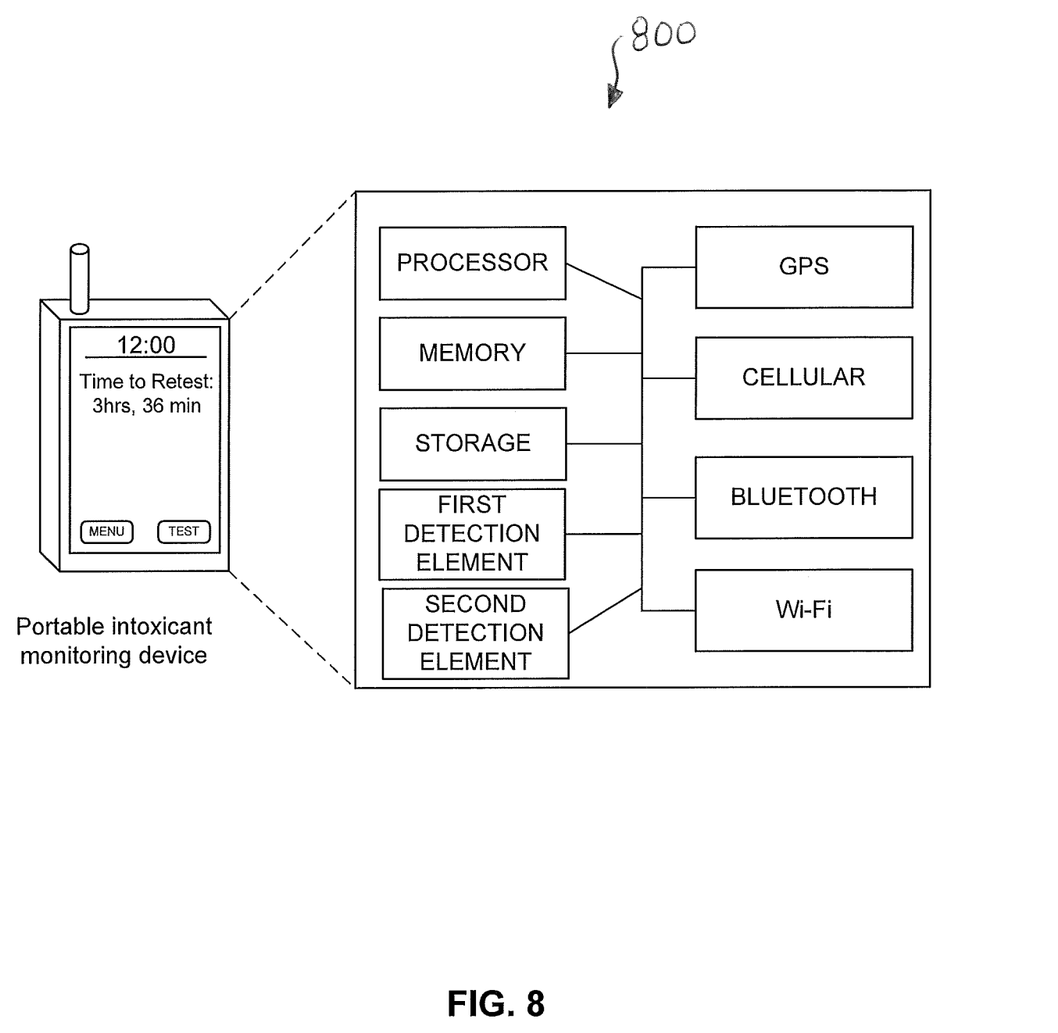
FIG. 8 is a schematic of an intoxicant monitoring system, according to an embodiment.

FIG. 8 shows a schematic of a home monitoring system or portable intoxicant monitoring system 800, such as may be used to ensure compliance with a court order requiring a user to be tested regularly to prove the user does not use a prohibited substance, such as alcohol or marijuana/THC. Although traditional "home monitoring" systems were tied to the user's home telephone line and required the user to be home at certain times (such as every eight hours) to complete a test, a portable intoxicant monitoring device such as is shown in FIG. 8 enables the user to work an eight hour shift and take a lunch break without having to return home to complete a test, or to perform other activities that involve being away from home for eight hours or more.

In operation, the portable intoxicant monitoring device of FIG. 8 can execute a software program on a processor to periodically prompt the user to undergo a breath intoxicant test or other test for an intoxicant. In one embodiment, the user proves identity, such as by having a photo taken while performing a test. The user then completes the test such as by blowing into an intoxicant sensor or engaging in another type of test. The results of the test can be communicated to a service provider's remote server such as by using a cellular modem comprising part of the portable intoxicant monitoring device, including data such as the test time, result, a photo of the user taking the test, and other such information.

The portable intoxicant monitoring device can include a first detection element and a second detection element. In various embodiments, the first detection element can be used to determine if the ambient air around the user will affect the results of a test, such as described in regards to FIG. 5. For example, if the user is located in a room with elevated levels of alcohol present in the air, and the device did not have information about the intoxicants in the ambient air, the device could give a false positive result. If elevated levels of alcohol are present in the ambient air and that is detected by one of the detection elements, the device may inform the user of its state, which may be referred to as an error state, false positive state or another state to indicate to the user that a change needs to be made, such as rolling down the car cabin windows, before an intoxicant measurement can be made. Without such a device state, the device would indicate a failed test, which could subject the user to penalties or a need to respond to inquiries from law enforcement. With such a device state, it is possible to give the user an opportunity to give a sample that can be assessed more accurately.

Figure 9:
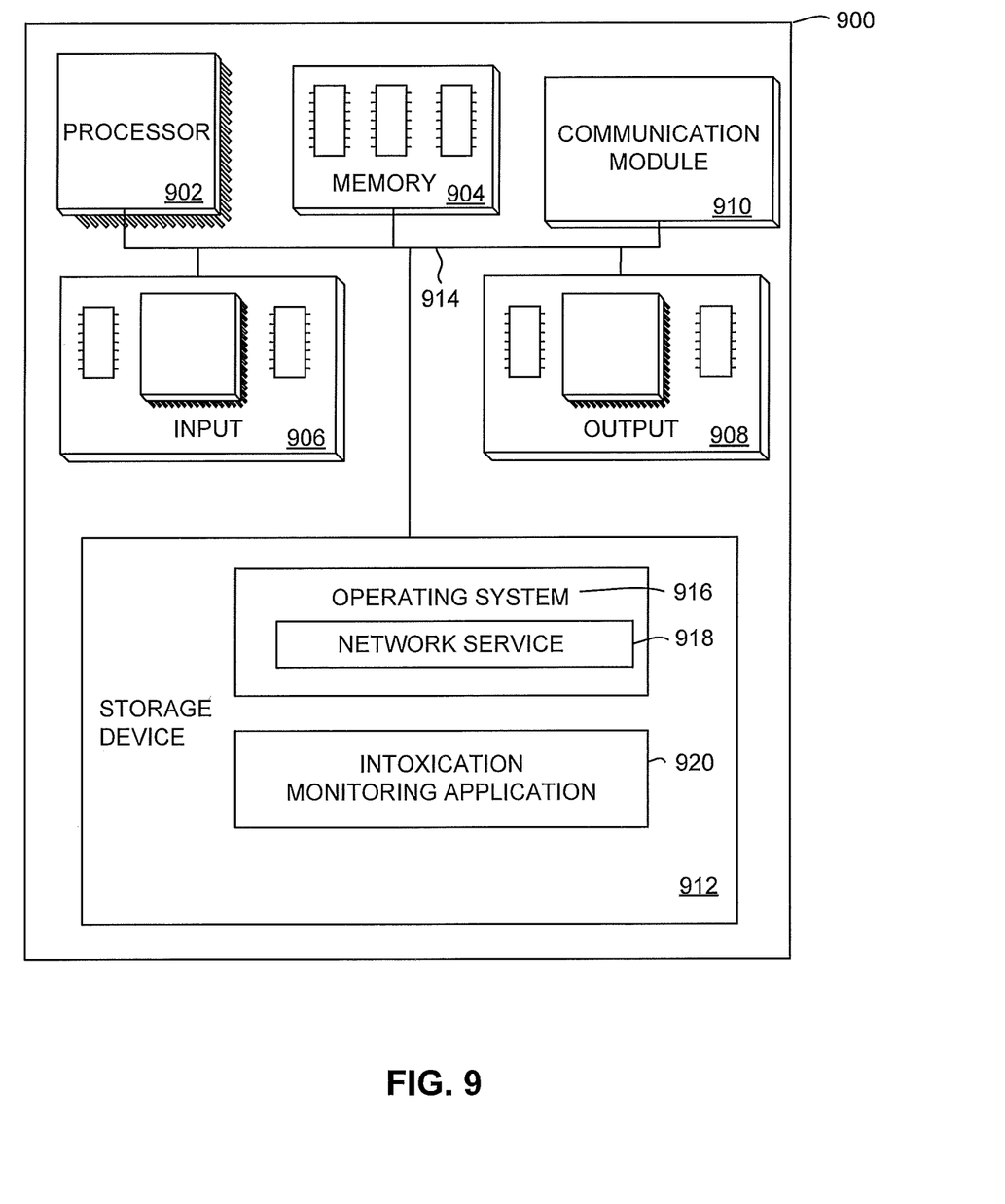
FIG. 9 is a schematic of a computerized system, according to an embodiment.

The systems and methods presented here may be implemented in part using a computerized device, such as a smartphone, handheld, or other computerized device, or including a computerized relay assembly, interposer, wireless relay module, or other computerized component. FIG. 9 shows a computerized intoxication monitoring system or component of a computerized intoxication interlock system, consistent with various examples described herein. FIG. 9 illustrates only one particular example of computing device 900, and other computing devices 900 may be used in other embodiments. Although computing device 900 is shown as a standalone computing device, computing device 900 may be any component or system that includes one or more processors or another suitable computing environment for executing software instructions in other examples, and need not include all of the elements shown here. A control module, relay box and detection unit as described herein are examples of components that can be implemented using computing devices such as computing device 900.

As shown in the specific example of FIG. 9, computing device 900 includes one or more processors 902, memory 904, one or more input devices 906, one or more output devices 908, one or more communication modules 910, and one or more storage devices 912. Computing device 900, in one example, further includes an operating system 916 executable by computing device 900. The operating system includes in various examples services such as a network service 918. One or more applications, such as an intoxication monitoring application 920 are also stored on storage device 912, and are executable by computing device 900.

Each of components 902, 904, 906, 908, 910, and 912 may be interconnected (physically, communicatively, and/or operatively) for inter-component communications, such as via one or more communications channels 914. In some examples, communication channels 914 include a system bus, network connection, inter-processor communication network, or any other channel for communicating data. Applications such as intoxication monitoring application 920 and operating system 916 may also communicate information with one another as well as with other components in computing device 900.

Processors 902, in one example, are configured to implement functionality and/or process instructions for execution within computing device 900. For example, processors 902 may be capable of processing instructions stored in storage device 912 or memory 904. Examples of processors 902 include any one or more of a microprocessor, a controller, a digital signal processor (DSP), an application specific integrated circuit (ASIC), a field-programmable gate array (FPGA), or similar discrete or integrated logic circuitry.

One or more storage devices 912 may be configured to store information within computing device 900 during operation. Storage device 912, in some examples, is known as a computer-readable storage medium. In some examples, storage device 912 comprises temporary memory, meaning that a primary purpose of storage device 912 is not long-term storage. Storage device 912 in some examples includes a volatile memory, meaning that storage device 912 does not maintain stored contents when computing device 900 is turned off. In other examples, data is loaded from storage device 912 into memory 904 during operation. Examples of volatile memories include random access memories (RAM), dynamic random access memories (DRAM), static random access memories (SRAM), and other forms of volatile memories known in the art. In some examples, storage device 912 is used to store program instructions for execution by processors 902. Storage device 912 and memory 904, in various examples, are used by software or applications running on computing device 900 such as intoxication interlock application 920 to temporarily store information during program execution.

Storage device 912, in some examples, includes one or more computer-readable storage media that may be configured to store larger amounts of information than volatile memory. Storage device 912 may further be configured for long-term storage of information. In some examples, storage devices 912 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Computing device 900, in some examples, also includes one or more communication modules 910. Computing device 900 in one example uses communication module 910 to communicate with external devices via one or more networks, such as one or more wireless networks. Communication module 910 may be a network interface card, such as an Ethernet card, an optical transceiver, a radio frequency transceiver, or any other type of device that can send and/or receive information. Other examples of such network interfaces include Bluetooth, 3G, 4G, LTE, 5G, Wi-Fi radios, and Near-Field Communications (NFC), and Universal Serial Bus (USB). In some examples, computing device 900 uses communication module 910 to wirelessly communicate with an external device such as via public network such as the Internet.

Computing device 900 also includes, in one example, one or more input devices 906. Input device 906, in some examples, is configured to receive input from a user through tactile, audio, or video input. Examples of input device 906 include a touchscreen display, a mouse, a keyboard, a voice responsive system, video camera, microphone or any other type of device for detecting input from a user.

One or more output devices 908 may also be included in computing device 900. Output device 908, in some examples, is configured to provide output to a user using tactile, audio, or video stimuli. Output device 908, in one example, includes a display, a sound card, a video graphics adapter card, or any other type of device for converting a signal into an appropriate form understandable to humans or machines. Additional examples of output device 908 include a speaker, a light-emitting diode (LED) display, a liquid crystal display (LCD), or any other type of device that can generate output to a user.

Computing device 900 may include operating system 916. Operating system 816, in some examples, controls the operation of components of computing device 900, and provides an interface from various applications such intoxication interlock application 920 to components of computing device 900. For example, operating system 916, in one example, facilitates the communication of various applications such as intoxication monitoring application 920 with processors 902, communication unit 910, storage device 912, input device 906, and output device 908. Applications such as intoxication interlock application 920 may include program instructions and/or data that are executable by computing device 900. As one example, intoxication monitoring application 920 may include instructions that cause computing device 900 to perform one or more of the operations and actions described in the examples presented herein.

In various embodiments, the control module can be configured to receive a signal from the first and second detection elements indicating the level of intoxicant in the user. The control module can be further configured to selectively operate the second detection element based on the signal received from the first detection element, and to indicate whether the level of intoxicant in the user's breath measured from at least one of the first and second detection elements exceeds a threshold. The control module can be further configured to selectively restrict operation of a vehicle based on whether the level of intoxicant in the user exceeds a threshold.

In various embodiments, the control module is configured to receive a signal from the first and second detection elements indicating the level of intoxicant in the user's breath. The control module can be configured to measure the signal from the first detection element before taking a sample with the second element. The control module can avoid taking a breath sample using the second detection element if the signal from the first detection element indicates a level of intoxicant in the user's breath that would contaminate the second detection element, such as being over a contamination threshold. In various embodiments, a contamination threshold can be equivalent to the level of intoxicant that could contaminate the second detection element to result in an inaccurate subsequent reading, such as when the second detection element includes a fuel cell.

In some embodiments, the first detection element can be less susceptible to contamination than the second detection element, such as when the second detection element is a fuel cell. In some embodiments, contamination can include a fuel cell memory effect, such as where subsequent tests conducted by a fuel cell are effected by previous tests that were conducted by the fuel cell.

In some embodiments, the system can include a self-calibrating test device or detection element, such as described in greater detail in U.S. patent application Ser. No. 12/504,714, filed Jul. 17, 2009, and titled "Ignition Interlock Breathalyzer," to Walter et al. and hereby incorporated by reference. In some embodiments, the system can be calibrated with a calibration station as described in U.S. patent application Ser. No. 15/261,253, filed Mar. 25, 2018, titled "Secure Data Handling in a Breath Alcohol Calibration Station" to DeVries et al. and Ser. No. 15/261,231 filed, Mar. 25, 2018, titled "Reference Gas Management in a Breath Alcohol Calibration Station", which are both hereby incorporated by reference.

In various embodiments, the control module is operable to measure the signal from the first detection element to monitor an environment around the system, such as vehicle cabin air, for contamination before prompting the user to perform a test and taking a sample with the second detection element. In some examples, the air around the system can be contaminated with alcohol, such as from a user washing windows. Conducting a test while the environment around the system, such as the vehicle cabin air, is contaminated could result in the user testing for a higher level of intoxicant in the user than he/she actually has. In various embodiments, the control module can be configured to delay a test or conduct a retest if an environment signal, such as a vehicle cabin signal, exceeds a threshold.

In some embodiments, the control module is operable to measure the signal from the first detection element before taking a sample with the second element, and to take a sample using the second element when the signal from the first element indicates that the breath being sampled is deep lung breath.

Examples of intoxicants that could be monitored by the intoxicant monitoring system include alcohol, marijuana, THC, Methamphetamine, prescription drugs, cocaine, heroin, psychedelic drugs or stimulants. In an embodiment, the intoxicant is ethanol. Examples of how to monitor for intoxicants include testing the user's breath using a fuel cell alcohol detector, a MOS alcohol detector, and an infrared alcohol detector. Examples of how to monitor for intoxicants include testing the user's breath, blood, sweat, or other body substance.

The second sensor in some examples has greater accuracy than the first sensor in that it performs some aspect of sensing the desired intoxicant in a way that is better or more useful than the first sensor. In a more detailed example, the precision with which the second sensor is able to measure the level of intoxicant, such as breath ethanol, is greater than the precision of the first sensor. In another example, the specificity to a specific intoxicant of interest, such as breath ethanol, is greater than the specificity of the first sensor. For example, the first sensor may detect breath ethanol but also be susceptible to detecting methanol vapor, paint thinner, or other vapors not of interest often found in a vehicle cabin, while the second sensor is less susceptible to these vapors not of interest, and therefore has greater specificity for the specific intoxicant of breath ethanol.

In various embodiments, the first detection element can be a continuous read detection element. The signal can be continuous such that the detection element is configured to provide or output the level of intoxicant for the air that just passed through or by the detection element. In some embodiments, the control module 112 can evaluate the continuous signal to differentiate between different portions of the sample. For example when the sample is a user's breath, the initial portion of the sample can have different characteristics than a later portion of the sample, such as when the later portion of the sample is from is deep lung air and the initial portion of the sample is from the user's mouth or throat. A continuous read detection element can include a sensor that is capable of taking at least a minimum number of readings/second. In some examples, a continuous read sensor does not required a defined volume for a sample, or the sample can continuously flow through or passed the sensor. Examples of continuous read sensors include MOS and IR sensors. In contrast, fuel cells are generally considered not be continuous read sensors.

In various embodiments, the first detection element can include a metal oxide sensor. In various embodiments, the first detection element can include a semiconductor sensor. In various embodiments, the first detection element can include an infrared (IR) sensor. In various embodiments, the second detection element can include a fuel cell.

In some embodiments, the first detection element and the second detection element differ from each other in an operational attribute, such as warm-up time, time needed to rest between evaluating samples, and operating temperature.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this technology pertains. All publications and patent applications are herein incorporated by reference to the same extent as if each individual publication or patent application was specifically and individually indicated by reference.

The technology has been described with reference to various specific and preferred embodiments and techniques. However, it should be understood that many variations and modifications may be made while remaining within the spirit and scope of the technology.

The invention claimed is:

1. A breath intoxicant monitoring system, comprising:
   a first detection element operable to detect a level of an intoxicant in a user's breath, the first detection element operable to provide a continuous signal indicating a level of intoxicant in a user's breath;
   a second detection element operable to detect a level of the intoxicant in the user's breath, the second detection element comprising a different type of element than the first detection element, where the second detection element has greater accuracy than the first detection element; and
   a control module operable to receive a signal from the first and second detection elements indicating the level of intoxicant in the user's breath, to measure the signal from the first detection element before taking a sample with the second detection element, to selectively operate the second detection element based on the signal received from the first detection element, avoid taking a breath sample using the second detection element if the signal from the first detection element indicates a level of intoxicant in the user's breath exceeding a threshold, and to indicate whether the level of intoxicant in the user's breath measured from at least one of the first and second detection elements exceeds a threshold.

2. The breath intoxicant monitoring system of claim 1, the control module further operable to selectively restrict operation of a vehicle based on whether the level of intoxicant in the user's breath measured from at least one of the first and the second detection elements exceeding a threshold.

3. The breath intoxicant monitoring system of claim 1, wherein the first detection element comprises one of the group consisting of a metal oxide sensor, a complementary metal oxide sensor, a semiconductor sensor, and an infrared (IR) sensor.

4. The breath intoxicant monitoring system of claim 1, wherein the second detection element comprises a fuel cell.

5. The breath intoxicant monitoring system of claim 1, wherein the control module is operable to take a sample using the second detection element when the signal from the first detection element indicates that the breath being sampled is deep lung breath.

6. The breath intoxicant monitoring system of claim 1, wherein the control module is operable to measure an environment signal from the first detection element to monitor air surrounding the system for contamination before prompting a user to perform a test and taking a sample with the second detection element.

7. The breath intoxicant monitoring system of claim 6, wherein the control module is further operable to delay a test or a retest if the environment signal exceeds a threshold.

8. The breath intoxicant monitoring system of claim 1, wherein the breath intoxicant monitoring system comprises an ignition interlock system or a home monitoring system.

9. The breath intoxicant monitoring system of claim 1, wherein greater accuracy comprises greater specificity to the intoxicant.

10. A breath intoxicant monitoring system, comprising:
    a first detection element operable to detect a level of an intoxicant in a user's breath, the first detection element operable to provide a signal indicating the level of the intoxicant in the user's breath;
    a second detection element operable to detect a level of the intoxicant in the user's breath, the second detection element comprising a fuel cell, wherein the first detection element is less susceptible to contamination than a fuel cell; and
    a control module operable to receive a signal from the first and second detection elements indicating a level of intoxicant in the user's breath, to measure the signal from the first detection element before taking a sample with the second detection element and to avoid taking a breath sample using the second detection element if the signal from the first detection element indicates a level of intoxicant in the user's breath that would contaminate the second detection element, and to indicate whether the level of intoxicant in the user's breath measured from at least one of the first and second detection elements exceeds a threshold.

11. The breath intoxicant monitoring system of claim 10, wherein the control module is further operable to selectively restrict operation of a vehicle based on the level of the intoxicant in the user's breath measured from at least one of the first and the second detection elements exceeding a threshold.

12. The breath intoxicant monitoring system of claim 10, wherein the intoxicant is ethanol, and the first detection element comprises a semiconductor sensor.

13. A method of operating a breath intoxicant monitoring system, comprising:
   detecting a level of an intoxicant in a user's breath using a first detection element operable to provide a continuous signal indicating a level of intoxicant;
   receiving in a control module a signal from the first detection element indicating the level of intoxicant in the user's breath before taking a sample with a second detection element,
   selectively operating via the control module a second detection element operable to detect a level of intoxicant in the user's breath based on the signal received from the first detection element and avoiding taking a breath sample using the second detection element if the signal from the first detection element indicates a level of intoxicant in the user's breath that would contaminate the second detection element, wherein the second detection element comprises a fuel cell, the first detection element comprises a different type of element than a fuel cell, wherein the first detection element is less susceptible to contamination than a fuel cell, where the second detection element has greater accuracy than the first detection element; and
   indicating whether the level of intoxicant in the user's breath measured from at least one of the first and second detection elements exceeds a threshold.

14. The method of operating a breath intoxicant monitoring system of claim 13, further comprising selectively restricting operation of a vehicle based on the level of intoxicant in the user's breath measured from at least one of the first and the second detection elements exceeding a threshold.

15. The method of operating a breath intoxicant monitoring system of claim 13, wherein the intoxicant is ethanol, the first detection element comprises a semiconductor sensor, and the second detection element comprises a fuel cell.

16. The method of operating a breath intoxicant monitoring system of claim 13, wherein selectively operating the second detection element comprises taking a breath sample using the second detection element when the signal from the first detection element indicates that the breath being sampled is deep lung breath.

17. The method of operating a breath intoxicant monitoring system of claim 13, wherein the second detection element comprises a fuel cell, wherein the first detection element is less susceptible to contamination than a fuel cell, wherein selectively operating the second detection element comprises measuring an environment signal from the first detection element to monitor air around the system for contamination before prompting the user to perform a test and taking a sample with the second detection element.

* * * * *